(12) United States Patent
Hasegawa et al.

(10) Patent No.: US 8,611,493 B2
(45) Date of Patent: Dec. 17, 2013

(54) X-RAY FLUORESCENCE ANALYZER AND X-RAY FLUORESCENCE ANALYSIS METHOD

(75) Inventors: Kiyoshi Hasegawa, Chiba (JP); Yutaka Ikku, Chiba (JP); Hideki Takiguchi, Chiba (JP)

(73) Assignee: SII Nanotechnology Inc., Chiba (JP)

( * ) Notice: Subject to any disclaimer, the term of this patent is extended or adjusted under 35 U.S.C. 154(b) by 208 days.

(21) Appl. No.: 13/174,058

(22) Filed: Jun. 30, 2011

(65) Prior Publication Data

US 2012/0051507 A1    Mar. 1, 2012

(30) Foreign Application Priority Data

Aug. 31, 2010    (JP) ................ 2010-193167

(51) Int. Cl.
*G01N 23/223*    (2006.01)
(52) U.S. Cl.
USPC ............................................. 378/44
(58) Field of Classification Search
None
See application file for complete search history.

(56) References Cited

U.S. PATENT DOCUMENTS

| | | | | |
|---|---|---|---|---|
| 5,969,603 | A * | 10/1999 | Wang | 340/471 |
| 6,038,280 | A | 3/2000 | Rössiger et al. | |
| 6,802,186 | B2 * | 10/2004 | Holmes et al. | 62/187 |
| 6,859,517 | B2 * | 2/2005 | Wilson et al. | 378/47 |
| 7,796,726 | B1 * | 9/2010 | Gendreau et al. | 378/46 |
| 7,972,062 | B2 * | 7/2011 | Nicolosi et al. | 378/205 |
| 2005/0103577 | A1 * | 5/2005 | Warner | 187/317 |
| 2011/0051894 | A1 * | 3/2011 | Takahara | 378/86 |

FOREIGN PATENT DOCUMENTS

| | | |
|---|---|---|
| JP | 10-274518 A | 10/1998 |
| JP | 2006-329944 A | 12/2006 |

* cited by examiner

*Primary Examiner* — Hoon Song
*Assistant Examiner* — Danielle Fox
(74) *Attorney, Agent, or Firm* — Brinks Gilson & Lione

(57) ABSTRACT

The X-ray fluorescence analyzer (100) includes: an enclosure (10); a door (20) for putting the sample into and out of the enclosure; a height measurement mechanism (7) capable of measuring a height at the irradiation point; a moving mechanism control unit (9) for adjusting a distance between the sample and the radiation source as well as the X-ray detector based on the measured height at the irradiation point; a laser unit (7) for irradiating the irradiation point with a visible light laser beam; a laser start control unit (9) for irradiating the visible light laser beam by the laser unit (7) when the door is open state; and a height measurement mechanism start control unit (9) for starting the height measurement mechanism to measure the height at the irradiation point when the door is opened.

11 Claims, 9 Drawing Sheets

X-RAY FLUORESCENCE ANALYZER AND X-RAY FLUORESCENCE ANALYSIS METHOD

RELATED APPLICATIONS

This application claims priority under 35 U.S.C. §119 to Japanese Patent Application No. 2010-193167 filed on Aug. 31, 2010, the entire content of which is hereby incorporated by reference.

BACKGROUND OF THE INVENTION

1. Field of the Invention

The present invention relates to an X-ray fluorescence analyzer and an X-ray fluorescence analysis method for performing X-ray fluorescence analysis or the like of a surface of a sample.

2. Description of the Related Art

X-ray fluorescence analysis is used to perform qualitative analysis or quantitative analysis of a sample by irradiating the sample with an X-ray emitted from an X-ray source to detect, with an X-ray detector, a characteristic X-ray (fluorescent X-ray) emitted from the sample, and by obtaining a spectrum from energy of the characteristic X-ray. The X-ray fluorescence analysis enables the non-destructive and quick analysis of the sample, and therefore the X-ray fluorescence analysis is widely used in manufacturing process management, quality control, or the like. In recent years, precision and sensitivity have been increased in the X-ray fluorescence analysis, which enables trace measurement. Accordingly, the X-ray fluorescence analysis is expected to be more widely used as an analysis technique of detecting especially a harmful substance contained in a material, a composite electronic component, or the like.

By the way, in the conventional X-ray fluorescence analysis, it is necessary to manually adjust a focus (adjust height) while observing a sample in an optical manner so that a distance between the sample and the X-ray source (height in z direction) is a constant value, which lowers working efficiency. Therefore, there is disclosed a technology of setting the X-ray source and an optical system to be coaxial with each other so that the focus adjustment of a sample is performed by the optical system automatically (see Japanese Patent Application Laid-open No. Hei 10-274518 (reference numeral 39 of FIG. 1)).

In addition, in the conventional X-ray fluorescence analysis, it is necessary to adjust an X-ray irradiation position by moving the sample in the apparatus in the x-y direction while observing the sample in the optical manner, which also lowers the working efficiency. Therefore, there is disclosed a technology of irradiating the sample with a laser beam emitted from a laser disposed in the vicinity of the X-ray source so that the X-ray irradiation position can be observed as a laser spot by the naked eye for facilitating the positioning (see Japanese Patent Application Laid-open No. 2006-329944 (reference numeral 9 of FIG. 1)).

However, when the technology described in Japanese Patent Application Laid-open No. 2006-329944 is used, if the laser beam is emitted also while the sample is being optically observed, the laser beam may form a bright spot that disturbs the observation or tires the eye of an operator. In addition, the work of manually turning off the laser in this case is troublesome and lowers the working efficiency.

On the other hand, when the distance between the sample and the X-ray source is adjusted by an automatic focusing device, there is a problem that an adjustment range is narrow (10 mm level) due to the focal depth.

SUMMARY OF THE INVENTION

The present invention has been made to solve the above-mentioned problems, and an object thereof is to provide an X-ray fluorescence analyzer and an X-ray fluorescence analysis method, which are superior in working efficiency and capable of measuring a sample safely.

In order to achieve the above-mentioned object, an X-ray fluorescence analyzer according to the present invention includes: a radiation source for irradiating an irradiation point on a sample with radiation; an X-ray detector for detecting a characteristic X-ray and a scattered X-ray, which are generated from the sample, to output a signal containing energy information of the characteristic X-ray and the scattered X-ray; an analyzer for analyzing the signal; a sample stage on which the sample is to be placed; a moving mechanism capable of relatively moving the sample on the sample stage and the radiation source as well as the X-ray detector; an enclosure that houses at least the radiation source, the sample stage, and the moving mechanism; a door that opens and closes an opening for putting the sample into and out of the enclosure; a height measurement mechanism capable of measuring a height of the sample at the irradiation point; a moving mechanism control unit for starting the moving mechanism based on the measured height at the irradiation point so as to adjust a distance between the sample and the radiation source as well as the X-ray detector; a laser unit for irradiating the irradiation point with a visible light laser beam; a door open/close detection unit for detecting an open/closed state of the door; a laser start control unit for starting the laser unit to emit the visible light laser beam when the door open/close detection unit detects that the door is opened, and stopping the laser unit when the door open/close detection unit detects that the door is closed; and a height measurement mechanism start control unit for starting the height measurement mechanism to measure the height at the irradiation point when the door open/close detection unit detects that the door is opened.

In this way, when the door is opened and the sample is placed on the sample stage in the enclosure, the visible light laser beam is emitted, and hence the irradiation point can be observed as a laser spot by the naked eye so that positioning of the sample can be facilitated. Further, because the irradiation by the visible light laser beam is stopped after the positioning of the sample, a bright spot of the visible light laser beam does not enter the eye of the operator when the sample is observed after the positioning. Thus, the observation is not disturbed, or the eye of the operator is not tired.

The laser unit may also function as the height measurement mechanism.

In this way, by using the emitted laser beam for measuring the height at the irradiation point, height information can be obtained simultaneously with the irradiation of the laser spot for positioning. Therefore, it is not necessary to manually adjust the distance between the sample and the X-ray source, thereby improving working efficiency. In addition, because the irradiation of the laser spot and the measurement of the height information are performed by a single laser unit, the apparatus can be compact and simplified, and the adjustment range of the distance between the sample and the X-ray source can be widened.

The laser start control unit may start the laser unit to measure the height at the irradiation point with the visible light laser beam when the door open/close detection unit detects that the door is closed and when it is detected that the moving mechanism has been started, and may stop the laser unit when it is detected that the moving mechanism has been stopped.

According to this structure, when the sample moves in at least one of X, Y, and Z directions, the distance between the sample and the radiation source as well as the X-ray detector is readjusted. Therefore, even if the distance or the focus varies only by a little change of the irradiation point when the sample is moved as in the case of the sample with an uneven surface, for example, the distance or the focus is automatically adjusted so that the X-ray analysis can be accurately performed.

The laser unit may include a first laser unit for emitting the visible light laser beam and a second laser unit for emitting an invisible light laser beam except the visible light laser beam, the second laser unit may also function as the height measurement mechanism, and the laser start control unit may start the first laser unit to emit the visible light laser beam when the door open/close detection unit detects that the door is opened, and may stop the first laser unit when the door open/close detection unit detects that the door is closed.

According to this structure, when the door is opened, the visible light laser beam is emitted, and hence the irradiation point can be observed as a laser spot by the naked eye so that the positioning of the sample can be facilitated. On the other hand, when the door is closed to observe the sample after the positioning, the invisible light laser beam, which is invisible to the operator, is used to measure the height. Thus, the height can be measured without disturbing the observation and tiring the eye of the operator.

The moving mechanism control unit may stop the moving mechanism when the height at the irradiation point becomes a predetermined threshold value or smaller.

According to this structure, when the irradiation point (namely, the surface of the sample) becomes close to each component of the X-ray fluorescence analyzer (the radiation source, the X-ray detector, or the like), the movement of the sample is stopped. Therefore, it is possible to prevent a malfunction that the sample contacts or collides with each component of the X-ray fluorescence analyzer.

It is preferred that an optical axis of the radiation emitted from the radiation source be coaxial with an optical axis of the laser unit, and that the radiation and the visible light laser beam emitted from the laser unit irradiate the sample.

According to this structure, even if the irradiation position of the radiation moves from a standard position to the height at the irradiation point, the optical axis of the laser unit does not change. Therefore, the laser spot for the positioning can be accurately irradiated at the irradiation point.

It is preferred that the X-ray fluorescence analyzer according to the present invention further include: an observation system for observing the sample; a focus switching drive mechanism for switching a focus of the observation system; and an observation system focus control unit for starting the focus switching drive mechanism, based on the height at the irradiation point measured by the height measurement mechanism, to adjust a focal position of the observation system.

According to this structure, a variation of the focal position of the observation system due to the movement of the sample can be automatically adjusted based on the height at the irradiation point. Therefore, it is not necessary for the operator to manually perform the focus adjustment of the observation system, thereby improving the working efficiency.

It is preferred that an optical axis of the radiation emitted from the radiation source, an optical axis of the observation system, and an optical axis of the laser unit be coaxial with one another, and that the radiation and the visible light laser beam emitted from the laser unit irradiate the sample.

According to this structure, even if the irradiation position of the radiation moves from a standard position to the height at the irradiation point, the optical axis of the laser unit does not change. Therefore, the laser spot for the positioning can be accurately irradiated at the irradiation point. In addition, even if the irradiation position of the radiation moves from the standard position to the height at the irradiation point, the optical axis of the observation system does not change. Therefore, the sample can be observed easily.

The X-ray fluorescence analyzer according to the present invention may further include: a mirror for setting the optical axis of the laser unit to be coaxial with the optical axis of the radiation; and a beam splitter for setting the optical axis of the radiation, the optical axis of the laser unit, and the optical axis of the observation system to be coaxial with one another.

According to this structure, the X-ray fluorescence analyzer can be made compact and simplified.

The height measurement mechanism may be capable of measuring the height at the irradiation point in a state where the sample is placed on the sample stage.

According to this structure, the height at the irradiation point can be measured in the state where the sample is placed on the sample stage. Therefore, an offset from an actual irradiation position of the radiation can be eliminated.

According to the present invention, there is provided an X-ray fluorescence detection method to be used in an X-ray fluorescence analyzer, the X-ray fluorescence analyzer including: a sample stage on which a sample is to be placed; a moving mechanism capable of relatively moving the sample on the sample stage and a radiation source as well as an X-ray detector; an enclosure that houses at least the radiation source, the sample stage, and the moving mechanism; and a door that opens and closes an opening for putting the sample into and out of the enclosure, for irradiating an irradiation point on the sample with radiation from the radiation source so as to detect a characteristic X-ray and a scattered X-ray, which are generated from the sample, with the X-ray detector for outputting a signal containing energy information of the characteristic X-ray and the scattered X-ray and for analyzing the signal, the X-ray fluorescence detection method including: a laser start controlling step of emitting a visible light laser beam when the door is detected to be opened, and stopping the emission of the visible light laser beam when the door is detected to be closed; an irradiation point height measuring step of measuring a height at the irradiation point when the door is detected to be opened; and a moving mechanism controlling step of starting the moving mechanism based on the measured height at the irradiation point to adjust a distance between the sample and the radiation source as well as the X-ray detector.

The X-ray fluorescence detection method according to the present invention may further include an observation system focus adjustment step of adjusting a focal position of an observation system for observing the sample based on the measured height at the irradiation point.

According to the present invention, in X-ray fluorescence analysis, the working efficiency is superior and the sample can be measured safely.

DETAILED DESCRIPTION OF THE PREFERRED EMBODIMENTS

Hereinafter, embodiments of the present invention are described with reference to the drawings. In each of the drawings referred to in the following description, each component is appropriately changed in scale for illustration in a recognizable manner.

Figure 1:
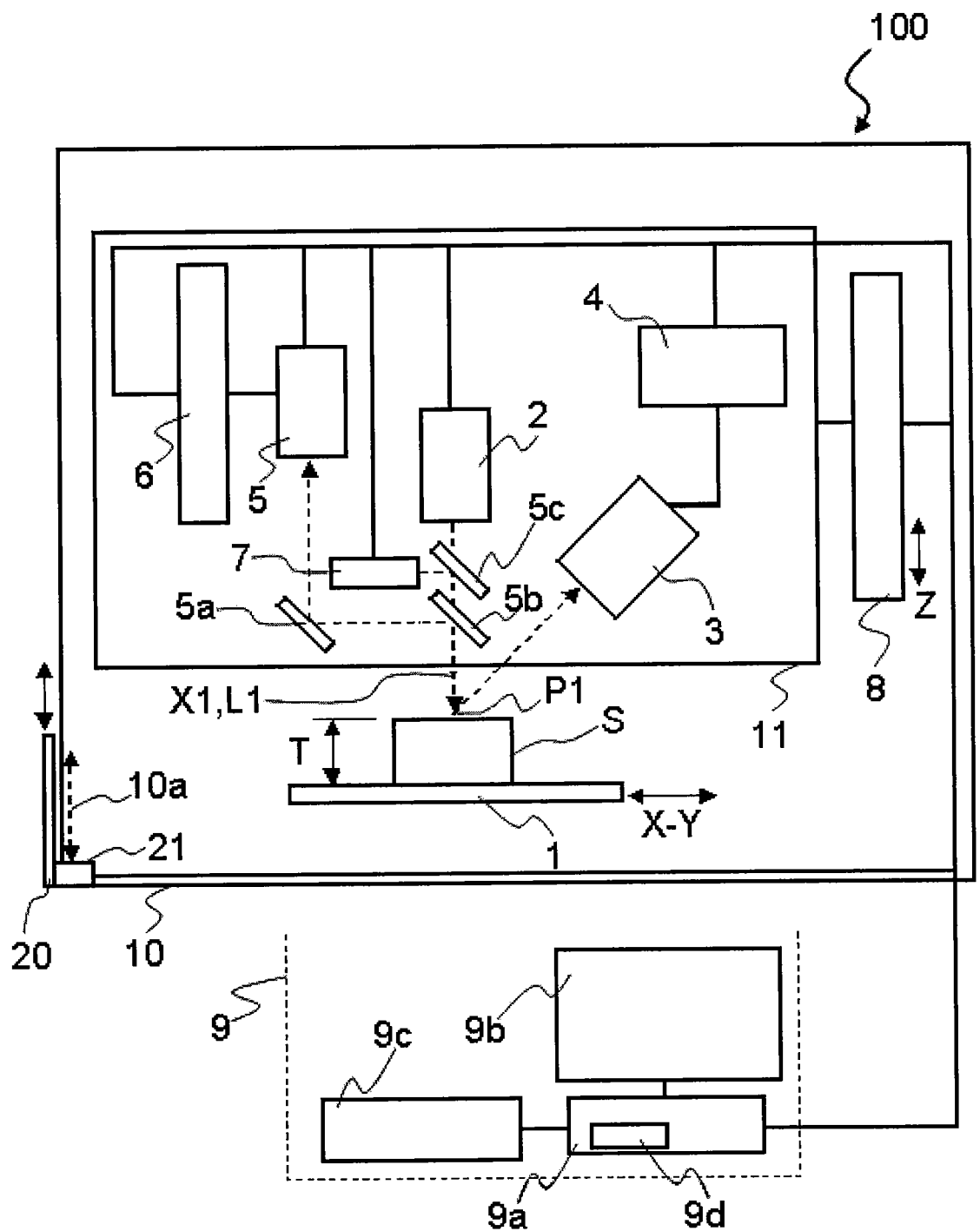
FIG. 1 is a block diagram illustrating a structure of an X-ray fluorescence analyzer according to a first embodiment of the present invention.

FIG. 1 is a block diagram illustrating a structure of an X-ray fluorescence analyzer 100 according to a first embodiment of the present invention. The X-ray fluorescence analyzer 100 is an energy dispersive X-ray fluorescence analyzer, for example, which includes a sample stage 1 on which a sample S is placed, an X-ray tube (radiation source) 2, an X-ray detector 3, an analyzer 4, an observation system 5, a focus switching drive mechanism 6, a laser unit 7, a measurement head moving mechanism 8, and a control computer 9 (corresponding to "moving mechanism control unit", "laser start control unit", "height measurement mechanism start control unit", and "observation system focus control unit" in claims).

In addition, each component of the X-ray fluorescence analyzer 100 (except the control computer 9) has a structure for preventing leakage of X-ray to the outside of the apparatus. Further, an enclosure 10 is provided with an opening 10a so that the sample S is put into or out of the enclosure 10 through the opening 10a. The opening 10a is provided with a door 20, which opens and closes the opening 10a. The open or closed state of the door 20 is detected by a door open/close detection unit 21 constituted of a door open/close sensor and the like. The door open/close detection unit 21 is connected to the control computer 9, and detection information of the door open/close detection unit 21 is sent to the control computer 9. As the door open/close sensor, a photomicrosensor can be used. In addition, in the present invention, it is possible to adopt a structure in which the inside of the X-ray fluorescence analyzer 100 can be decompressed, or a structure without pressure adjustment.

The X-ray tube 2 is disposed above the sample stage 1 and irradiates any irradiation point P1 on the sample S with a primary X-ray (radiation) X1. The X-ray tube 2, for example, emits as the primary X-ray X1 an X-ray, which is generated by the fact that thermoelectrons generated from a filament (positive electrode) of the tube are accelerated by a voltage applied between the filament (positive electrode) and a target (negative electrode) to thereby smash against the target of W (tungsten), Mo (molybdenum), Cr (chromium), or the like, from a window of a beryllium foil or the like.

The X-ray detector 3 is disposed above the sample stage 1 and is apart from the X-ray tube 2. The X-ray detector 3 detects a characteristic X-ray and a scattered X-ray generated from the sample S, and outputs a signal containing energy information of the characteristic X-ray and the scattered X-ray. The X-ray detector 3, for example, includes a semiconductor detection element (for example, Si (silicon) element which is a pin-structure diode) (not shown) disposed to an incident window of the X-ray, and when one X-ray photon enters, a current pulse corresponding to the one X-ray photon is generated. A momentary current value of the current pulse is proportional to energy of the incident characteristic X-ray. Further, the X-ray detector 3 is set so as to convert the current pulse generated in the semiconductor detection element into a voltage pulse and amplify and output the voltage pulse as a signal.

The analyzer 4 is connected to the X-ray detector 3 and analyzes the above-mentioned signal. The analyzer 4 is, for example, a pulse height analyzer (multi-channel analyzer) for obtaining a pulse height of the voltage pulse from the signal to generate an energy spectrum.

The observation system 5 is an optical system that includes an optical microscope and the like, and can display an image of the sample S illuminated by illumination means such as a light bulb (not shown), as image data. The observation system 5 is disposed above the sample stage 1 and is apart from the X-ray tube 2. The observation system 5 is constituted of, for example, a mirror 5a, a beam splitter 5b, and an optical microscope and an observation camera that can view and take a magnified image of the sample S via the beam splitter 5b. Further, the image light of the sample S is sent along an optical axis of the primary X-ray X1 and is reflected by the beam splitter 5b in a lateral direction, and is further reflected by the mirror 5a upward so as to enter the optical microscope and the observation camera from below.

The focus switching drive mechanism 6 moves the observation system 5 along the optical axis direction so as to switch the focal position. The movement of the observation system 5 by the focus switching drive mechanism 6 can be performed by using an actuator such as a ball screw or a belt connected to or incorporated in the observation system 5 and the focus switching drive mechanism 6 and by drive of a stepping motor or the like.

Figure 2:
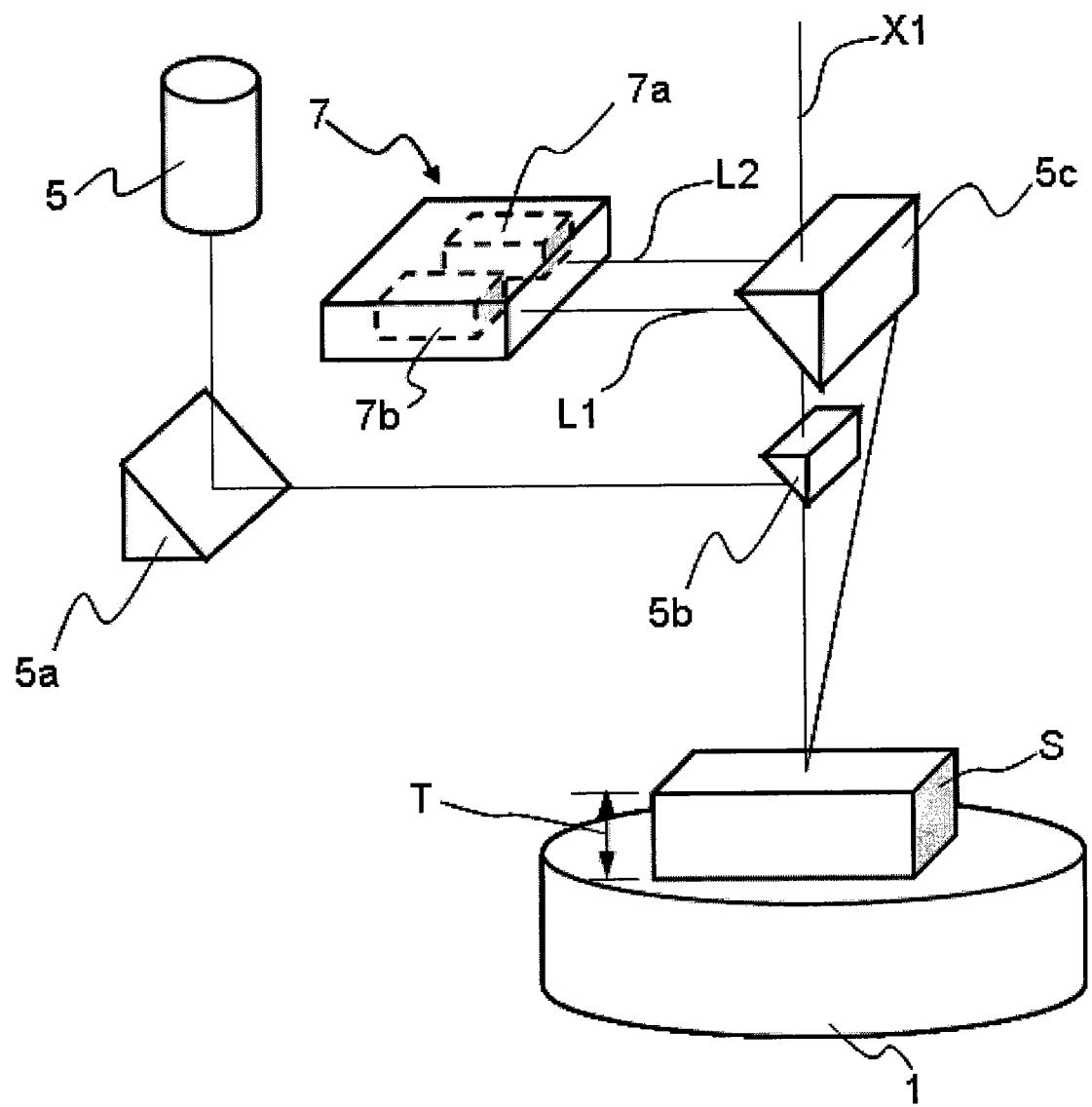
FIG. 2 is a perspective view illustrating arrangement of a radiation source, an observation system, and a laser unit.

The laser unit 7 is disposed above the sample stage 1 and below the X-ray tube 2, and is apart from the X-ray tube 2. The laser unit 7 can emit a visible light laser beam in a lateral direction, so as to measure a sample height T at any irradiation point P1 on the sample S. As illustrated in FIG. 2, the laser unit 7 includes, for example, a light emitting portion 7a constituted of a semiconductor laser element, a light receiving portion 7b constituted of a CCD, an optical position sensitive detector (PSD), or a linear image sensor, and a light projection lens and a light receiving lens (not shown). As the laser unit 7, a reflective type sensor utilizing triangulation (triangulation laser displacement sensor) can be used. The laser displacement sensor is available in the market. Note that, "visible light" means light having a wavelength defined in JIS-Z8120, in which the short wavelength side is 360 to 400 nm, and the long wavelength side is 760 to 830 nm.

Here, as illustrated in FIG. 2, the optical axis of the observation system 5 is set so that the light is reflected by the mirror 5a and the beam splitter 5b to be coaxial with the optical axis of the primary X-ray X1. Similarly, an optical axis of a primary laser beam L1 is set so that the light is reflected downward by a mirror 5c to be coaxial with the optical axis of the primary X-ray X1. In other words, the beam splitter 5b and the mirror 5c are disposed on the optical axis of the primary laser beam L1 so that the optical axis of the primary laser beam L1 and the optical axis of the observation system 5 become coaxial with the optical axis of the primary X-ray X1. Note that, the beam splitter 5b and the mirror 5c are movable and can retreat from a path (optical axis) of the primary X-ray X1 while the analysis by the X-ray is being performed.

In this way, the irradiation point P1 is irradiated with the primary laser beam L1. Further, when the irradiation point P1 is irradiated with the primary laser beam L1, a secondary laser beam L2 is generated, which returns to the light receiving portion 7b. Therefore, by detecting a sensing state of the secondary laser beam L2, distance information (height T of the sample S from the sample stage 1) can be obtained, and this output is sent to the control computer 9. Note that, the optical axis of the secondary laser beam L2 is offset from the optical axis of the primary X-ray X1 so that the light enters the light receiving portion 7b without passing through the beam splitter 5b, in order that laser intensity of the secondary laser beam L2 coming back from the sample S be not attenuated.

Note that, in this embodiment, the sample stage 1 is an XY stage that is movable horizontally in the two-dimensional direction in the state where the sample S is placed on the sample stage 1. On the other hand, a relative movement of the sample S in the height direction (Z direction) is performed by the measurement head moving mechanism 8. In other words, the X-ray tube 2, the X-ray detector 3, the analyzer 4, the observation system 5, the focus switching drive mechanism 6, and the laser unit 7 are integrally installed in a measurement head 11, and the measurement head moving mechanism 8 can move along the propagation direction of the primary X-ray X1 (height direction (Z direction)) by the measurement head 11. Therefore, when the measurement head 11 is moved forward and backward in the Z direction relatively to the sample stage 1, the distance between the sample S and the X-ray tube 2 as well as the X-ray detector 3 is adjusted. The movement of the sample stage 1 and the movement of the measurement head 11 by the measurement head moving mechanism 8 can be performed by using an actuator such as a ball screw or a belt connected thereto or incorporated therein and by drive of a stepping motor or the like.

The sample stage 1 and the measurement head moving mechanism 8 correspond to "moving mechanism" in claims.

The control computer 9 includes a control main unit 9a that determines X-ray intensity corresponding to a specific element from an energy spectrum sent from the analyzer 4, a display unit 9b that displays a result of the analysis based on the X-ray intensity, and an operating portion 9c for inputting various instructions such as a position of the irradiation point P1 or conditions for the analysis. In addition, the control main unit 9a also has a function of communication control with the focus switching drive mechanism 6 and the measurement head moving mechanism 8. The control main unit 9a includes a CPU, a ROM, a RAM, a recording medium such as a hard disk, which are well known, and a control circuit board 9d for starting and stopping the laser unit 7.

Figure 3:
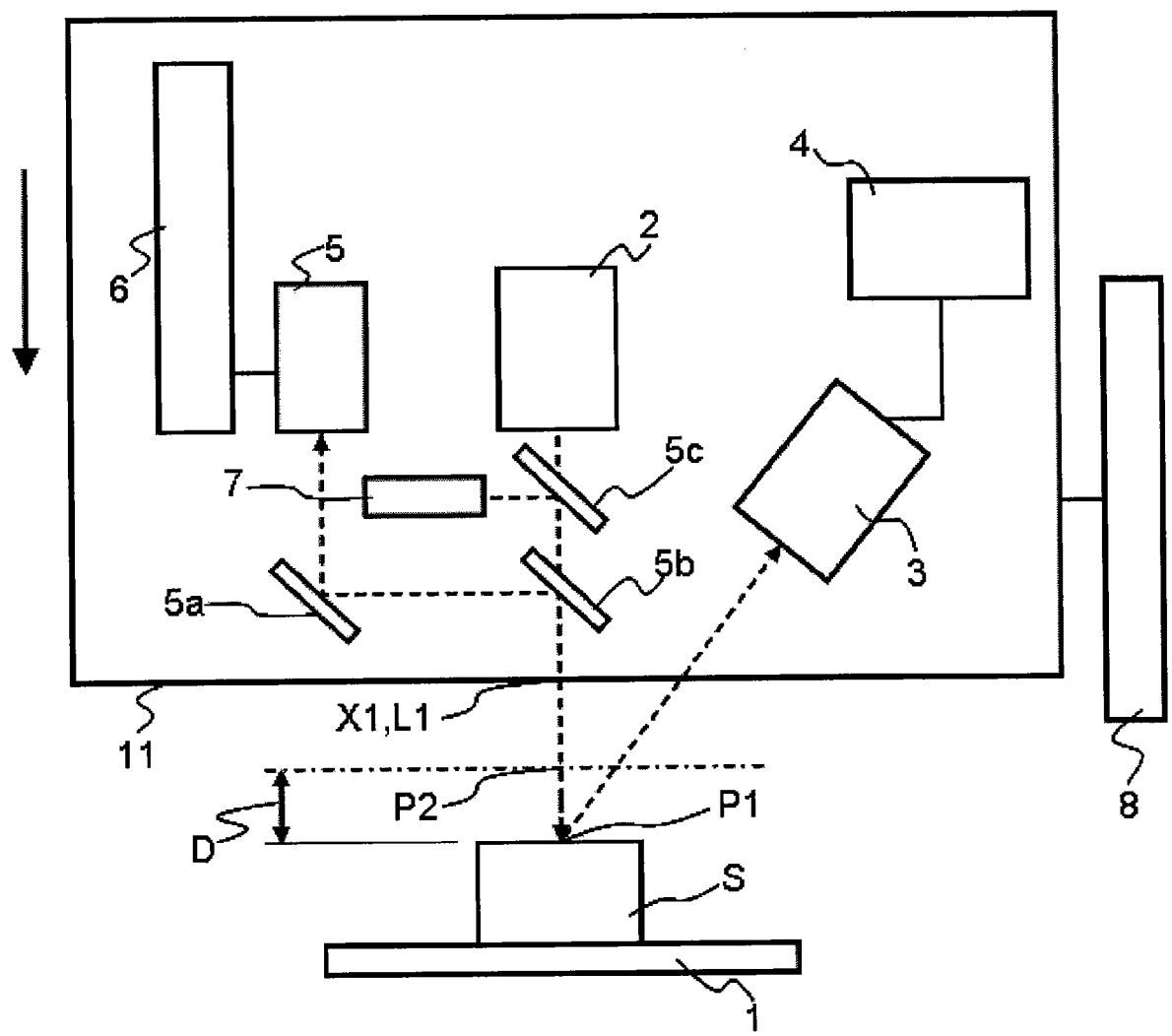
FIG. 3 is a diagram illustrating how to relatively move a sample, the radiation source, and an X-ray detector.

In addition, the control computer 9 adjusts the distance between the sample S and the X-ray tube 2 as well as the X-ray detector 3 as illustrated in FIG. 3. First, the control computer 9 obtains information of the height T from the laser unit 7. Further, if the height T is lower than the height of a standard irradiation position P2 of the primary X-ray X1, the control computer 9 starts the measurement head moving mechanism 8 to cancel a distance of a difference D between T and P2. Thus, the irradiation point P1 is aligned with P2.

Here, the standard irradiation position P2 is an intersection of an irradiation axis of the primary X-ray X1 from the X-ray tube 2 and a direction of the X-ray detector 3 (at the maximum sensitivity). Further, the standard irradiation position P2 (its height) is stored in the control computer 9 in advance.

Figure 4:
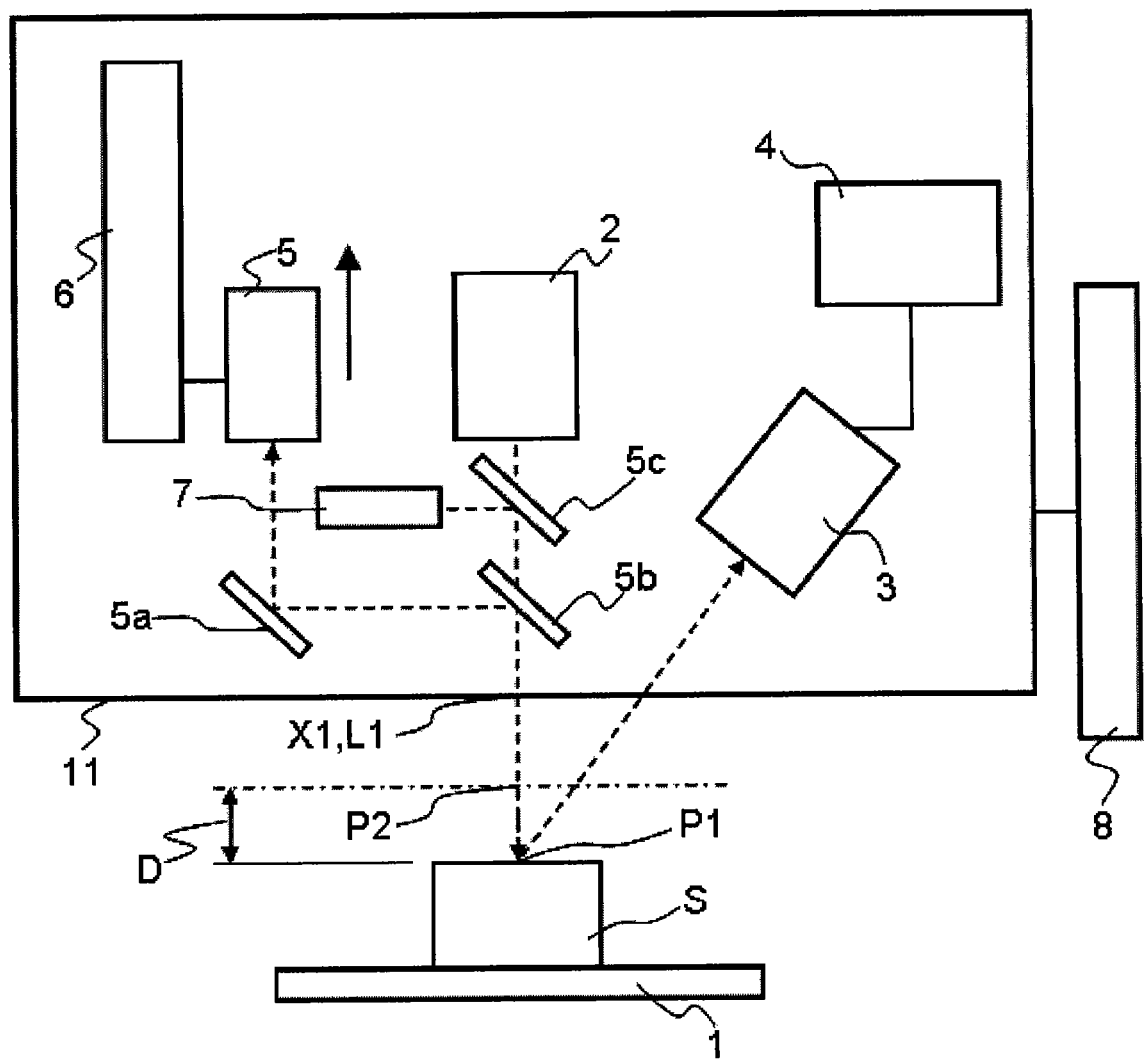
FIG. 4 is a diagram illustrating how to adjust a focal position of the observation system.

Further, the control computer 9 also adjusts the focal position of the observation system 5 simultaneously based on the height T obtained by the laser unit 7, as illustrated in FIG. 4. In other words, the focus switching drive mechanism 6 is started to adjust the focal position of the observation system 5 so as to cancel the above-mentioned distance of the difference D. In this way, the operator is not required to manually adjust the focal position of the observation system 5 for observing the sample S. The start control of the focus switching drive mechanism 6 by the control computer 9 can be performed, for example, by determining a position where an image contrast of the observation system 5 becomes the maximum as the focal position.

Note that, the control computer 9 stores the standard irradiation position P2 in advance also as an original position (not shown) of the focus switching drive mechanism 6, and can determine the height T based on a displacement of the focus switching drive mechanism 6 from the original position, while the observation system 5 can function also as distance measuring means. The displacement of the focus switching drive mechanism 6 can be determined by calculating, for example, the number of input pulses of the stepping motor for driving or the number of output pulses from an encoder. Further, the control computer 9 is adapted to correct a parameter such as an X-ray irradiation distance used for quantitative calculation in the control computer 9, in accordance with the difference D calculated from the height T determined by the observation system 5 as the distance measuring means.

Note that, the focus switching drive mechanism 6 and the measurement head moving mechanism 8 can be controlled by the control computer 9 simultaneously or independently of each other.

Figure 5:
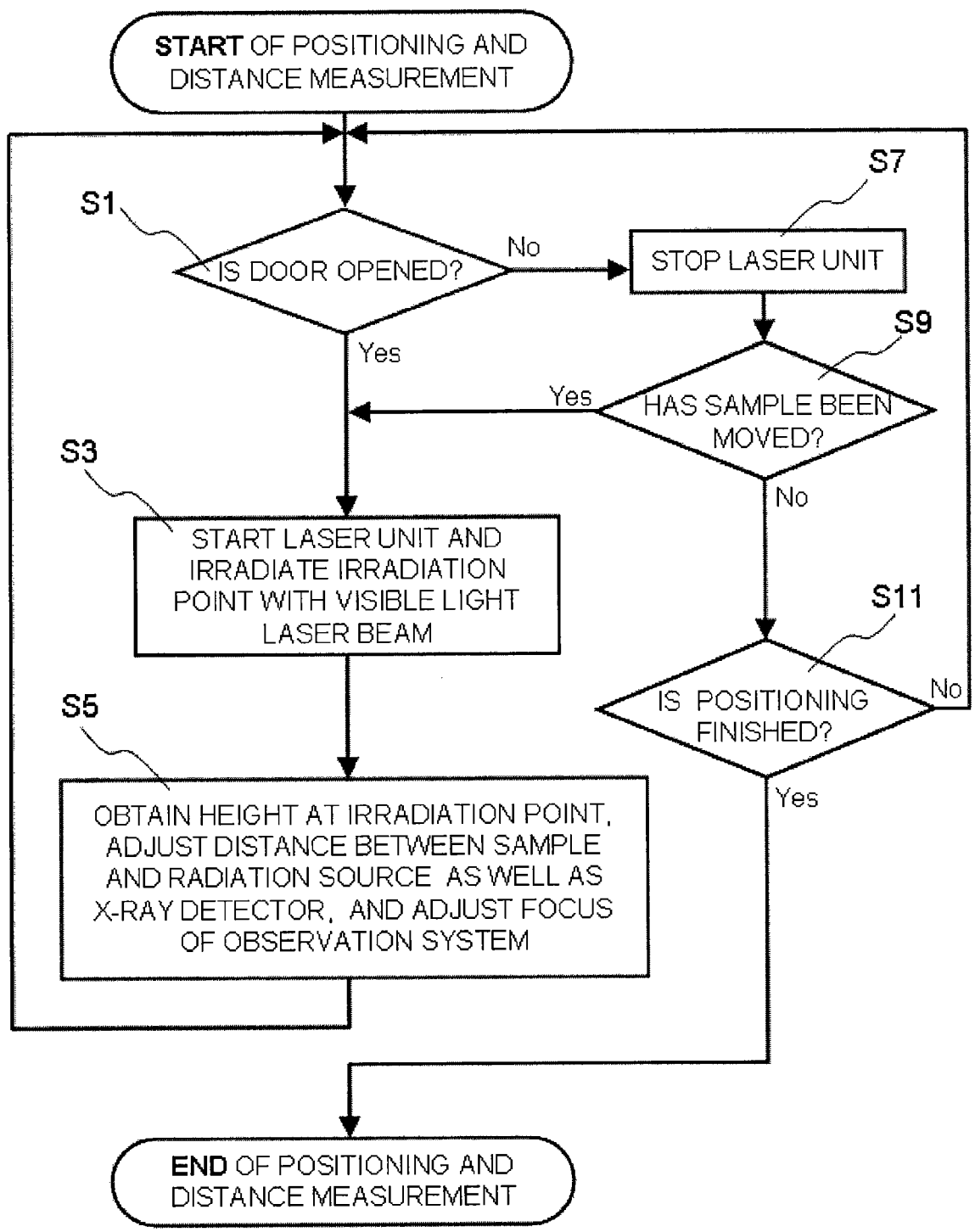
FIG. 5 is a flow chart for positioning and distance measurement performed by a control computer.

Next, the X-ray analysis using the X-ray fluorescence analyzer 100 is described with reference to FIG. 5. FIG. 5 illustrates a flow chart of the control performed by the control computer 9 (flow chart for positioning and distance measurement).

First, the control computer 9 obtains detection information from the door open/close detection unit 21, and determines whether or not the door 20 is opened (Step S1). If the door 20 is opened, it means that the operator is placing a new sample S on the sample stage 1. Therefore, if the determination is "Yes" in Step S1, the control computer 9 starts the laser unit 7 so that the irradiation point P1 is irradiated with the visible light laser beam (Step S3). The laser unit 7 receives the secondary laser beam L2 generated from the irradiation point P1, obtains information of the distance (height T of the sample S from the sample stage 1), and sends the information to the control computer 9.

The control computer 9 calculates the difference D based on the obtained information of the height T at the irradiation point P1, and starts the measurement head moving mechanism 8 so that the difference D is canceled (Step S5). In this way, the irradiation point P1 is aligned with P2, and the distance between the sample S and the radiation source 2 is adjusted. Simultaneously, the control computer 9 starts the focus switching drive mechanism 6 so that the difference D is canceled, and adjusts the focus of the observation system 5 (Step S5). After Step S5 is finished, the process flow returns to Step S1.

Next, if the door 20 is closed, it means that the placement of the sample S on the sample stage 1 has been finished, and that the operator is observing the surface of the sample S with the observation system 5 to check the point of the X-ray analysis. If the visible light laser beam is emitted in this period of time, the laser beam forms a bright spot and disturbs the observation or tires the eye of the operator. Therefore, if the determination is "No" in Step S1, the control computer 9 stops the laser unit 7 so that the emission of the visible light laser beam is turned off (Step S7).

Next, the control computer 9 determines whether or not the sample S has moved in at least one of X, Y, and Z directions (Step S9). If the sample S has moved in at least one of X, Y, and Z directions, it means that the operator has moved the point of the X-ray analysis while observing the surface of the sample S with the observation system 5. Therefore, it is necessary to readjust the distance and the focus that have been adjusted in the above-mentioned Steps S3 and S5. Therefore, if the determination is "Yes" in Step S9, the process flow returns to Step S3, in which the control computer 9 readjusts the distance and the focus. Note that, it is possible to determine whether or not the sample S has moved by drive of the actuator such as a stepping motor for starting the sample stage 1 and the measurement head moving mechanism 8.

In addition, if the sample S is moved after the door 20 is closed, the operator observes the surface of the sample S while seeing the bright spot of the visible light laser beam. However, compared with the case where the door 20 is opened to place the sample S first on the sample stage 1, the movement amount of the sample S is small. Therefore, the time period of seeing the bright spot of the visible light laser beam is short, and the influence to the operator is small.

On the other hand, if the determination is "No" in Step S9, it means that a new point of the X-ray analysis is fixed. Therefore, the process is finished when the operator instructs "to end the positioning" using the operating portion 9c ("Yes" in Step S11). In addition, if the determination is "No" in Step S11, it means that the positioning is not finished, and the process flow returns to Step S1.

As described above, the process flow for positioning and distance measurement is finished, and the X-ray analysis can be performed. The X-ray analysis itself is a known technique. First, the X-ray tube 2 emits the primary X-ray X1 to the sample S, and the generated characteristic X-ray and scattered X-ray are detected by the X-ray detector 3. The X-ray detector 3 that has detected the X-ray sends the signal to the analyzer 4. The analyzer 4 extracts the energy spectrum from the signal and outputs the energy spectrum to the control computer 9. The control main unit 9a determines the X-ray intensity corresponding to a specific element from the energy spectrum received from the analyzer 4, and a result of the analysis is displayed on the display unit 9b.

Figure 6:
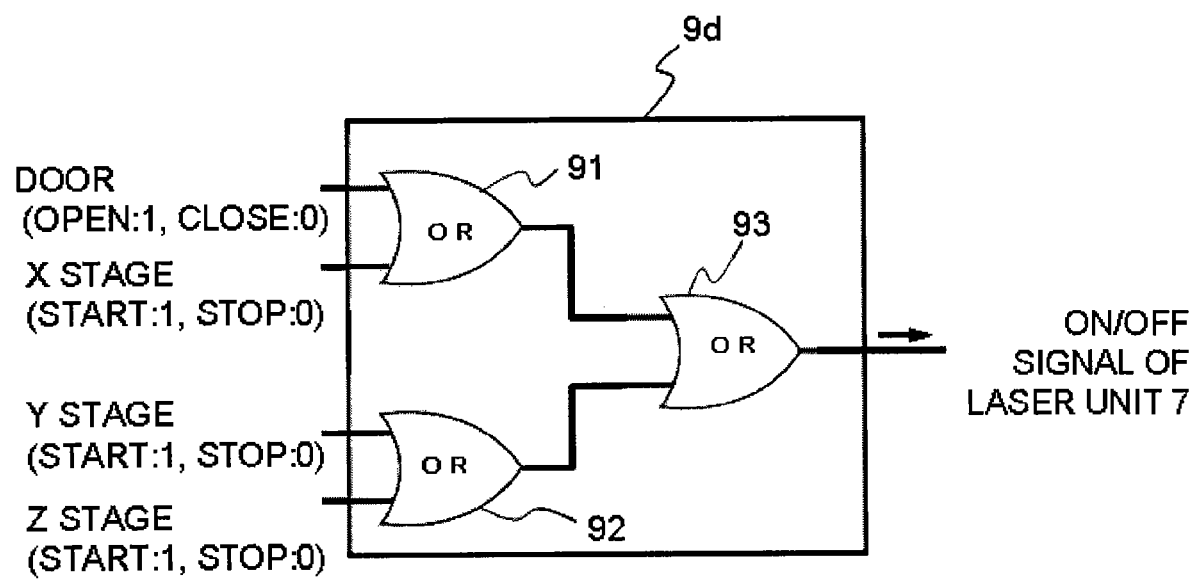
FIG. 6 is a block diagram illustrating a logical structure of a control circuit board that controls start and stop of the laser unit.

FIG. 6 is a block diagram illustrating a logical structure of the control circuit board 9d that controls start and stop of the laser unit 7. The control circuit board 9d includes three transistors 91 to 93 each of which is constituted of an OR circuit. Outputs of the transistors 91 and 92 are supplied to the transistor 93. The transistor 91 is supplied with an input whose value "1" means the open state of the door 20 and an input whose value "1" means a state where a movement (motion) of the sample S has occurred in the X direction. In addition, the transistor 92 is supplied with inputs whose values "1" mean states where movements (motions) of the sample S have occurred in the Y direction and in the Z direction, respectively.

Therefore, when the door 20 is opened and the sample S has moved in at least one of X, Y, and Z directions, the transistor 93 outputs the signal ("1") for starting the laser unit 7.

Note that, the start and stop of the laser unit 7 may be realized by the above-mentioned control circuit board 9d or the condition thereof may be determined by software.

As described above, according to the X-ray fluorescence analyzer of this embodiment, when the door 20 is opened and the sample S is placed on the sample stage 1 in the enclosure 10, the primary laser beam L1 that is visible light is emitted. Therefore, the irradiation point P1 can be checked as a laser spot by the naked eye, and positioning of the sample S can be facilitated. Further, because the emission of the primary laser beam L1 is stopped after the positioning of the sample S, the bright spot of the visible light laser beam does not enter the eye of the operator when the operator observes the sample after the positioning. Thus, the observation is not disturbed, or the eye of the operator is not tired.

Further, by using the emitted primary laser beam L1 for measuring the height T at the irradiation point P1, it is possible to obtain information of the height T at the same time as irradiation of the laser spot for the positioning. Thus, it is not necessary to manually adjust the distance between the sample and the X-ray source, and hence working efficiency is improved. In addition, because the laser spot irradiation and the measurement of the information of the height T are performed using a single laser unit 7, the apparatus becomes compact and simple, and the adjustment range of the distance between the sample and the X-ray source is widened (100 mm level).

In addition, by simultaneously adjusting the focal position of the observation system 5 based on the obtained information of the height T, the operator is not required to manually adjust the focus of the observation system 5.

In addition, by measuring the height T using the laser unit 7, it is possible to correctly measure the height T of the sample S in a non-contact manner. Further, because the height T of the sample S is measured in the state where the sample S is placed on the sample stage 1 (state for X-ray analysis), it is possible to obtain the distance between the sample S and the X-ray tube 2 as well as the X-ray detector 3 during the analysis more accurately.

Further, when the sample S moves in at least one of X, Y, and Z directions, by readjusting the distance between the sample S and the X-ray tube 2 as well as the X-ray detector 3 and the focus of the observation system 5, the distance and the focus can be automatically adjusted so that the X-ray analysis can be performed accurately, even if the distance or the focus changes when the sample is moved to change the irradiation point slightly as in the case where the sample has an uneven surface.

Note that, it is preferred that the control computer (moving mechanism control unit) 9 perform control of stopping the moving mechanisms 1 and 8 when the height T at the irradiation point P1 becomes a predetermined threshold value or smaller. In this way, it is possible to prevent the sample S from contacting with a component such as the observation system 5 or the X-ray tube 2.

In addition, in the above-mentioned embodiment, the sample S is moved relatively so that the difference D is canceled and that the sample S is irradiated with the primary X-ray X1 at the standard irradiation position P2. However, in order to perform the X-ray analysis more simply (quickly), it is also possible to perform only the calculation of the difference D without moving the sample S relatively. In this case, the sample S is not moved relatively, but the sample S is irradiated with the primary X-ray X1 at the irradiation point P1 (its height T). The control computer 9 corrects a parameter to be used for calculation of the quantitative analysis according to the difference D from pulse height data of the energy spectrum obtained from the analyzer 4 at that time, and calculates the X-ray intensity corresponding to a specific element using the corrected value. It is needless to say that the focal position of the observation system 5 may be adjusted based on the difference D.

Here, when the irradiation position of the primary X-ray X1 is changed from the standard irradiation position P2 to the height at the irradiation point P1, a distance between the X-ray tube 2 and the irradiation point P1, a distance between the irradiation point P1 and the X-ray detector 3, and an angle between the direction of the X-ray detector 3 (detection direction) and the irradiation point P1 are changed. Accordingly, energy density and an irradiation region of the primary X-ray X1 that irradiates the sample S are changed. Specifically, intensities of the fluorescent X-ray and the scattered X-ray generated from the sample S are changed, or the intensities of the fluorescent X-ray and the scattered X-ray detected by the X-ray detector 3 are changed. Therefore, by correcting parameters such as the distance between the X-ray tube 2 and the irradiation point P1, the distance between the irradiation point P1 and the X-ray detector 3, and the angle between the direction of the X-ray detector 3 and the irradiation point P1 (hereinafter, also referred to as correction parameters), to thereby perform the quantitative analysis accurately.

In addition, the control computer 9 can store the height T at each irradiation point P1. In this case, by moving the sample stage 1 while the primary laser beam L1 irradiates the sample S, data of the height T in the two-dimensional direction of the sample S is obtained, and height variation in the two-dimensional direction of the sample (uneven shape) can be obtained.

Figure 7:
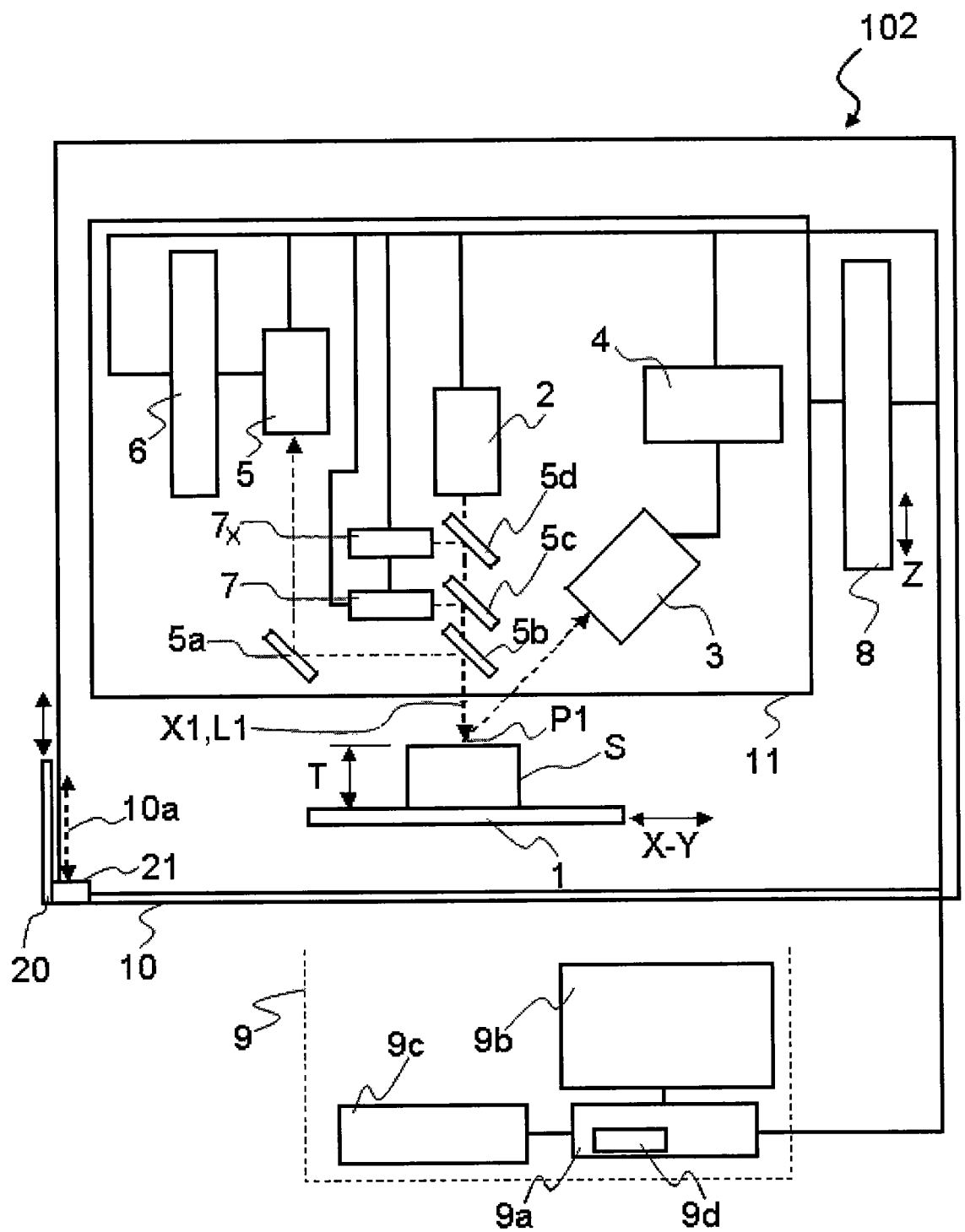
FIG. 7 is a block diagram illustrating a structure of an X-ray fluorescence analyzer according to a second embodiment of the present invention.

Next, an X-ray fluorescence analyzer 102 according to a second embodiment of the present invention is described with reference to FIG. 7. FIG. 7 is a block diagram illustrating a structure of the X-ray fluorescence analyzer 102. The X-ray fluorescence analyzer 102 is the same as the X-ray fluorescence analyzer 100 of the first embodiment except that a second laser unit 7x is added to the components of the X-ray fluorescence analyzer 100 and that the control flow (flow for positioning and distance measurement) performed by a control computer 9x is different. Therefore, the same component is denoted by the same numeral or symbol so that description thereof is omitted. In addition, in order to distinguish from the second laser unit 7x, the laser unit 7 is referred to as "first laser unit 7". The first laser unit 7 emits the visible light laser beam, while the second laser unit 7x emits an invisible light laser beam. The invisible light means light having a wavelength outside the wavelength range of the visible light. The second laser unit 7x may have the same structure as the first laser unit 7 (laser displacement sensor and the like).

In FIG. 7, the second laser unit 7x is disposed above the laser unit 7 and below the X-ray tube 2. The second laser unit 7x can emit the invisible light laser beam in the lateral direction, and the optical axis of the invisible light laser beam is set so that the invisible light laser beam is reflected downward by a mirror 5d to be coaxial with the optical axis of the primary X-ray X1. In other words, the mirror 5d is disposed on the optical axis of the primary laser beam L1 so that the optical axis of the invisible light laser beam becomes coaxial with the optical axis of the primary X-ray X1. However, the mirror 5d is movable and can retreat from a path (optical axis) of the primary X-ray X1 while the analysis by the X-ray is being performed.

In the second embodiment, when the door 20 is opened and the sample S is placed on the sample stage 1, the first laser unit 7 emits the visible light laser beam in the same manner as in the first embodiment. Therefore, the irradiation point P1 can be checked as a laser spot by the naked eye. On the other hand, the second laser unit 7x is used for readjusting the distance between the sample S and the X-ray tube 2 as well as the X-ray detector 3 and the focus of the observation system 5 when the sample S moves in at least one of X, Y, and Z directions after the door 20 is closed. In other words, the above-mentioned distance is measured using the invisible light laser beam while the operator observes the sample. Therefore, the distance and the focus can be readjusted while preventing the bright spot of the visible light laser beam from entering the eye of the operator.

Note that, the method of measuring the distance (height T) by the second laser unit 7x is the same as that by the first laser unit 7 as described above.

Figure 8:
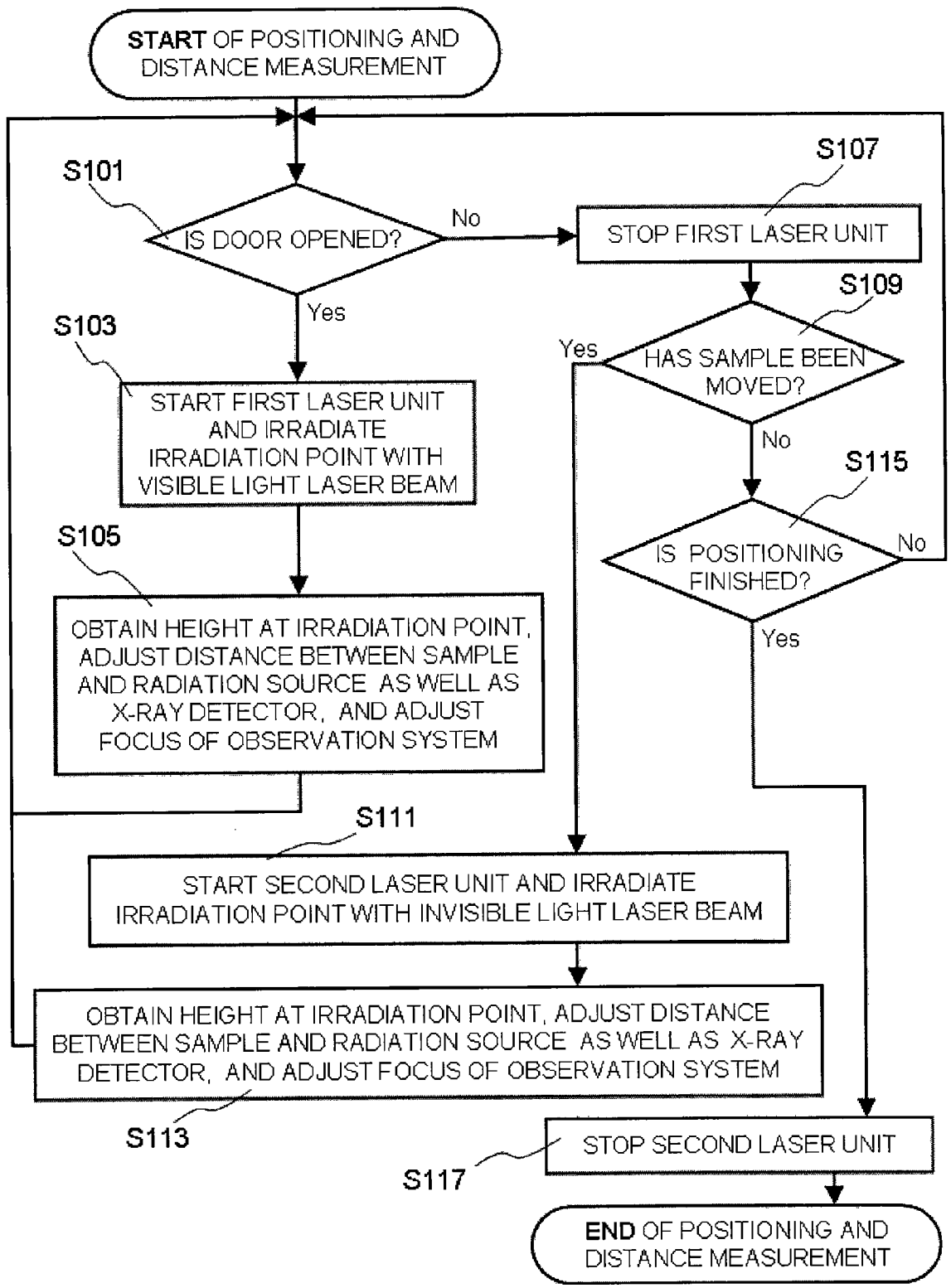
FIG. 8 is a flow chart for positioning and distance measurement performed by the control computer in the second embodiment.

FIG. 8 illustrates a control flow (flow for positioning and distance measurement) performed by the control computer 9x in the second embodiment.

First, the control computer 9x obtains detection information from the door open/close detection unit 21 to determine whether or not the door 20 is opened (Step S101). If the determination is "Yes" in Step S101, the control computer 9x starts the first laser unit 7 so that the visible light laser beam irradiates the irradiation point P1 (Step S103). The first laser unit 7 receives the secondary laser beam L2 generated from the irradiation point P1, and obtains information of the distance (height T of the sample S from the sample stage 1), which is sent to the control computer 9x.

The control computer 9x calculates the difference D based on the obtained information of the height T at the irradiation point P1, and starts the measurement head moving mechanism 8 so that the difference D is canceled (Step S105). In this way, the irradiation point P1 is aligned with P2, and the distance between the sample S and the radiation source 2 is adjusted. At the same time, the control computer 9x starts the focus switching drive mechanism 6 to cancel the difference D and adjust the focus of the observation system 5 (Step S105). After Step S105 is finished, the process flow returns to Step S101.

Next, if the determination is "No" in Step S101, the control computer 9x stops the first laser unit 7 and turns off the emission of the visible light laser beam (Step S107).

Note that, the process flow of Steps S101 to S107 is the same as that of Steps S1 to S7 in the first embodiment.

Next, the control computer 9x determines whether or not the sample S has moved in at least one of X, Y, and Z directions (Step S109). Here, if the determination is "Yes" in Step S109, the control computer 9x starts the second laser unit 7x so that the invisible light laser beam irradiates a new irradiation point P1 after the sample S has moved (Step S111). The second laser unit 7x receives the secondary laser beam L2 of the invisible light generated from the irradiation point P1, and obtains information of the distance (height T of the sample S from the sample stage 1), which is sent to the control computer 9x.

The control computer 9x calculates the difference D based on the obtained information of the height T at the irradiation point P1 and starts the measurement head moving mechanism 8 so that the difference D is canceled (Step S113). In this way, the irradiation point P1 is aligned with P2, and the distance between the sample S and the radiation source 2 is adjusted. At the same time, the control computer 9x starts the focus switching drive mechanism 6 so that the difference D is canceled, and adjusts the focus of the observation system 5 (Step S113). After Step S113 is finished, the process flow returns to Step S101.

As described above, if the determination is "Yes" in Step S109, the second laser unit 7x is started instead of the first laser unit 7. Thus, even if the operator changes the point of the X-ray analysis while observing the surface of the sample S using the observation system 5, a bright spot of the visible light laser beam is not generated, and hence an influence to the operator is suppressed. In addition, the readjustments to the distance between the sample S and the X-ray tube 2 as well as the X-ray detector 3 and the focus of the observation system 5 are performed using the invisible light laser beam. Therefore, the operator is not required to manually perform the readjustments similarly to the first embodiment.

On the other hand, if the determination is "No" in Step S109, it means that the new point of the X-ray analysis is fixed. Therefore, when the operator instructs "to end the positioning" using the operating portion 9c ("Yes" in Step S115), the control computer 9x stops the second laser unit 7x (Step S117), and finishes the process. In addition, if the determination is "No" in Step S115, it means that the positioning is not finished, and the process flow returns to Step S101.

Figure 9:
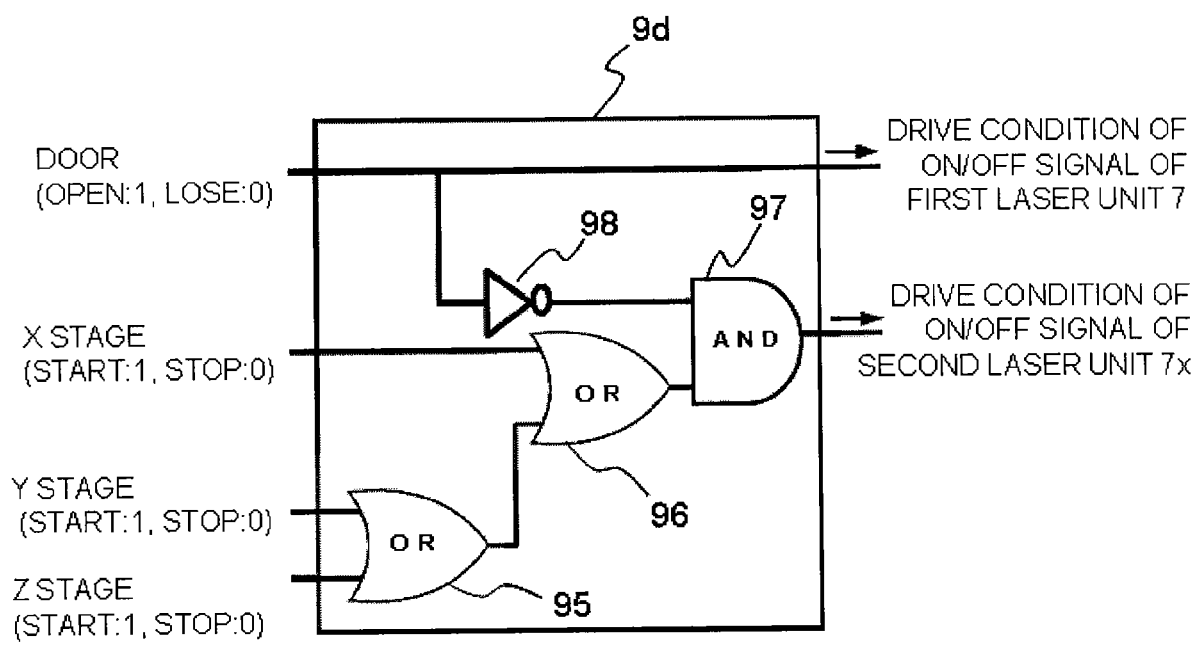
FIG. 9 is a block diagram illustrating a logical structure of the control circuit board that controls start and stop of first and second laser units in the second embodiment.

FIG. 9 is a block diagram illustrating a logical structure of the control circuit board 9d that controls start and stop of the first laser unit 7 and the second laser unit 7x in the second embodiment. The control circuit board 9d includes two transistors 95 and 96 each of which is constituted of an OR circuit, a transistor 97 constituted of an AND circuit, and a diode 98. An output of the transistor 95 and an input whose value "1" means a state where a movement (motion) of the sample S has occurred in the X direction are supplied to the transistor 96. In addition, outputs of the transistor 96 and the diode 98 are supplied to the transistor 97. Note that, the diode 98 is an element for inverting the signal logic.

The input whose value "1" means an open state of the door 20 is used directly as a condition for driving the ON/OFF signal of the first laser unit 7 and is supplied to the diode 98. The transistor 95 is supplied with inputs whose values "1" mean states where movements (motions) of the sample S have occurred in the Y direction and in the Z direction, respectively.

Therefore, when the door 20 is opened, the first laser unit 7 is started ("1"). On the other hand, if the sample S has moved in at least one of X, Y, and Z directions and the door 20 is closed, the transistor 97 outputs the signal ("1") for starting the second laser unit 7x.

Note that, the start and stop of the first laser unit 7 and the second laser unit 7x may be realized by the above-mentioned control circuit board 9d or the conditions thereof may be determined by software.

Note that, the technical scope of the present invention is not limited to the embodiments described above, which can be modified variously without deviating from the spirit of the present invention.

For instance, in the embodiments described above, the triangulation laser displacement sensor is used as the laser unit that functions as the height measurement mechanism for the sample S, but a linear regression laser displacement sensor may be used. In the case of the linear regression laser displacement sensor, the secondary laser beam returns on the same axis as the primary laser beam. Therefore, a mirror area can be reduced, and the adjustment mechanism can be simplified.

In addition, in the above-mentioned embodiments, the beam splitter 5b and the mirror 5c are movable and can retreat from the path of the primary X-ray X1 while the analysis is being performed so that the primary X-ray can irradiate the sample without attenuating intensity thereof. However, in the case of observing a state of the sample in real time while the primary X-ray is being emitted, the positions of the beam splitter 5b and the mirror 5c may be fixed. In this case, thicknesses of the beam splitter 5b and the mirror 5c are set so that the primary X-ray is transmitted through the beam splitter 5b and the mirror 5c without being attenuated as much as possible. In this way, the state of the sample can be observed in real time while the primary X-ray is being emitted.

Note that, it is preferred to use the laser unit also as the height measurement mechanism, but an ultrasonic sensor may be used.

In addition, in the above-mentioned embodiments, the inside of the enclosure is decompressed for the analysis, but it is also possible to perform the analysis not in the vacuum (or decompressed state).

Further, the X-ray fluorescence analyzer in the embodiments described above is an energy dispersive X-ray fluorescence analyzer, but may also be, for example, a wavelength dispersive X-ray fluorescence analyzer or a scanning electron microscope-energy dispersive X-ray spectrometer (SEM-EDS) capable of obtaining a secondary electron image by using an electron beam as a radiation beam to be irradiated.

In addition, the semiconductor detector is used as the X-ray detector in the embodiments described above, but a proportional counter may be used, and the present invention may be applied to a fluorescent X-ray thicknessmeter.

What is claimed is:

1. An X-ray fluorescence analyzer, comprising:
    a radiation source for irradiating an irradiation point on a sample with radiation;
    an X-ray detector for detecting a characteristic X-ray and a scattered X-ray, which are generated from the sample, to output a signal containing energy information of the characteristic X-ray and the scattered X-ray;
    an analyzer for analyzing the signal;
    a sample stage on which the sample is to be placed;
    a moving mechanism capable of relatively moving the sample on the sample stage and the radiation source as well as the X-ray detector;
    an enclosure that houses at least the radiation source, the sample stage, and the moving mechanism;
    a door that opens and closes an opening for putting the sample into and out of the enclosure;
    a moving mechanism control unit for starting the moving mechanism based on a measured height at the irradiation point so as to adjust a distance between the sample and the radiation source as well as the X-ray detector;
    a laser unit for irradiating the irradiation point with a visible light laser beam, the laser unit including a triangulation displacement sensor for measuring the height of the sample at the irradiation point and a first laser unit for emitting the visible light laser beam;
    a door open/close detection unit for detecting an open/closed state of the door;
    a laser start control unit for starting the laser unit to emit the visible light laser beam when the door open/close detection unit detects that the door is opened, and stopping the laser unit when the door open/close detection unit detects that the door is closed; and
    a height measurement mechanism start control unit for starting the laser unit to measure the height at the irradiation point when the door open/close detection unit detects that the door is opened.

2. An X-ray fluorescence analyzer according to claim 1, wherein the laser start control unit uses the laser unit and starts the laser unit to measure the height at the irradiation point with the visible light laser beam when the door open/close detection unit detects that the door is closed and when it is detected that the moving mechanism has been started, and stops the laser unit when it is detected that the moving mechanism has been stopped.

3. An X-ray fluorescence analyzer according to claim 1, wherein:
the laser unit further comprises a second laser unit for emitting an invisible light laser beam and wherein,
the laser start control unit starts the first laser unit to emit the visible light laser beam when the door open/close detection unit detects that the door is opened, and stops the first laser unit when the door open/close detection unit detects that the door is closed and uses the second laser unit to readjusts the distance between the sample and the radiation source during sample stage movement.

4. An X-ray fluorescence analyzer according to claim 1, wherein the moving mechanism control unit stops the moving mechanism when the height at the irradiation point becomes a predetermined threshold value or smaller.

5. An X-ray fluorescence analyzer according to claim 1, wherein an optical axis of the radiation emitted from the radiation source is coaxial with an optical axis of the laser unit, and the radiation and the visible light laser beam emitted from the laser unit irradiate the sample.

6. An X-ray fluorescence analyzer according to claim 1, further comprising:
an observation system for observing the sample;
a focus switching drive mechanism for switching a focus of the observation system; and
an observation system focus control unit for starting the focus switching drive mechanism, based on the height at the irradiation point measured by the height measurement mechanism, to adjust a focal position of the observation system.

7. An X-ray fluorescence analyzer according to claim 6, wherein:
an optical axis of the radiation emitted from the radiation source, an optical axis of the observation system, and an optical axis of the laser unit are coaxial with one another; and
the radiation and the visible light laser beam emitted from the laser unit irradiate the sample.

8. An X-ray fluorescence analyzer according to claim 7, further comprising:
a mirror for setting the optical axis of the laser unit to be coaxial with the optical axis of the radiation; and
a beam splitter for setting the optical axis of the radiation, the optical axis of the laser unit, and the optical axis of the observation system to be coaxial with one another.

9. An X-ray fluorescence analyzer according to claim 1, wherein the height measurement mechanism is capable of measuring the height at the irradiation point in a state where the sample is placed on the sample stage.

10. An X-ray fluorescence detection method, the X-ray fluorescence analyzer comprising:
a sample stage on which a sample is to be placed;
a moving mechanism capable of relatively moving the sample on the sample stage and a radiation source as well as an X-ray detector;
an enclosure that houses at least the radiation source, the sample stage, and the moving mechanism;
a laser unit including a triangulation displacement sensor for measuring a height of the sample at the irradiation point and a first laser unit for emitting a visible light laser beam; and
a door that opens and closes an opening for putting the sample into and out of the enclosure, for irradiating an irradiation point on the sample with radiation from the radiation source so as to detect a characteristic X-ray and a scattered X-ray, which are generated from the sample, with the X-ray detector for outputting a signal containing energy information of the characteristic X-ray and the scattered X-ray and for analyzing the signal,
the X-ray fluorescence detection method comprising:
a laser start controlling step of emitting the visible light laser beam when the door is detected to be opened, and stopping the emission of the visible light laser beam when the door is detected to be closed;
an irradiation point height measuring step of measuring a height at the irradiation point when the door is detected to be opened; and
a moving mechanism controlling step of starting the moving mechanism based on the measured height at the irradiation point to adjust a distance between the sample and the radiation source as well as the X-ray detector.

11. An X-ray fluorescence detection method according to claim 10, further comprising an observation system focus adjustment step of adjusting a focal position of an observation system for observing the sample based on the measured height at the irradiation point.

* * * * *